United States Patent [19]

Chu et al.

[11] Patent Number: 4,899,575

[45] Date of Patent: Feb. 13, 1990

[54] METHOD AND APPARATUS FOR DETERMINING VISCOSITY

[75] Inventors: Benjamin Chu, Setauket; Harbans S. Dhadwal, Westbury, both of N.Y.

[73] Assignee: Research Foundation of State University of New York, Albany, N.Y.

[21] Appl. No.: 226,300

[22] Filed: Jul. 29, 1988

[51] Int. Cl.[4] .............................................. G01N 11/06
[52] U.S. Cl. ....................................................... 73/55
[58] Field of Search .............................. 73/55, 861.95

[56] References Cited

U.S. PATENT DOCUMENTS

| | | | |
|---|---|---|---|
| 3,604,247 | 9/1971 | Gramain | 73/55 |
| 3,851,181 | 11/1974 | Heule | 250/577 |
| 3,908,129 | 9/1975 | Akers | 250/577 |
| 3,908,441 | 9/1975 | Virloget | 73/55 |
| 4,200,806 | 4/1980 | Walker et al. | 250/577 |
| 4,223,231 | 9/1980 | Sugiyama | 250/577 |
| 4,396,911 | 8/1983 | Motsinger et al. | 340/617 |
| 4,532,811 | 8/1985 | Miller, Jr. et al. | 73/861.95 |
| 4,566,337 | 1/1986 | Smart | 73/861.56 |
| 4,616,503 | 10/1986 | Plungis et al. | 73/55 |
| 4,648,263 | 3/1987 | Deysarkar et al. | 73/59 |

FOREIGN PATENT DOCUMENTS 1049787 10/1983 U.S.S.R. ................................... 73/55

OTHER PUBLICATIONS

Shvestka, M., *Methods of Investigation Automatic Capillary Viscometer*, In Polymer Sci. (USSR), vol. 16, No. 1, pp. 264–268, 1974.

Primary Examiner—Michael J. Tokar
Assistant Examiner—Joseph W. Roskos
Attorney, Agent, or Firm—Hoffmann & Baron

[57] ABSTRACT

A capillary viscometer is provided which includes a fiber-optic probe and a phototransistor which produces an output signal as a liquid meniscus falls through the field of view of a detecting fiber bundle. An analog circuit is employed for receiving the signal and starting or stopping a digital counter in response thereto. The circuit includes first and second differentiators and a zero detection portion for detecting zero value outputs from the second differentiator. The counter is started or stopped upon the generation of a triggering pulse at the time such zero value is detected.

17 Claims, 3 Drawing Sheets

METHOD AND APPARATUS FOR DETERMINING VISCOSITY

BACKGROUND OF THE INVENTION

The field of the invention relates to the determination of intrinsic viscosity through the use of a capillary viscometer or the like.

Presently known capillary viscometers include substantially transparent tubes through which flows the liquid whose viscosity is to be measured. The tube employed in connection with the viscometer is maintained at a constant temperature. Viscosity may be measured by determining the time in which it takes a given volume of liquid contained within the tube to flow between two points, such time being proportional to the viscosity of the liquid. A pair of light sources and corresponding receivers are provided for detecting the passage of the meniscus through these points.

Because conventional capillary viscometers using fiber-optic sensors can only measure flow times between selected points to a useful absolute accuracy of ± 0.01 seconds, it has remained a standard practice to make viscosity measurements as a function of concentration and then extrapolate the reduced viscosity to zero concentration to determine the intrinsic viscosity. The error involved in such extrapolation processes can be decreased by, for example, increasing the number of data points or increasing the measurement time. Such steps are disadvantageous in that they are very time consuming. Attempts have also been made to increase flow time accuracy by increasing the volume of the sample.

Conventional fiber-optic probes have been used to detect the presence of the fluid meniscus within the tube of a viscometer. Such probes include two optical fiber bundles, one for transmitting light to the capillary and the other for detecting the scattered or transmitted light at the liquid-air interface. A light sensitive element produces an output signal as the meniscus falls through the field of view of the detecting fiber bundle. This signal is used to start a counter. A second such element is used to stop the counter, thereby allowing the time elapsed between the two detection points to be measured. In order for the time to be accurately determined, however, the triggering of the counter must be done at precise and repeatable points. One of the most important considerations in the design of pulse shaping and timing circuits is therefore how to produce a suitable triggering point from the output signals in order to start and stop the counter.

One approach for providing an accurate trigger point has been to employ a threshold detection circuit. However, supply voltage fluctuations produce different saturation levels in the output signals, which in turn affect the time at which such signals reach the desired threshold levels. In addition, the threshold level will have a finite ripple.

SUMMARY OF THE INVENTION

It is an object of the invention to provide a method and apparatus for increasing the time resolution capability of a capillary viscometer.

It is another object of the invention to provide flow time measurements, over a wide range of polymer concentration, in capillary viscometers with a time resolution of ± 0.001 seconds, which enables small polymer (or particle) conformational changes to be observed.

Still another object of the invention is to provide a method and apparatus for estimating the intrinsic viscosity of a sample over a wide range of molecular weights by making flow time measurements at a single concentration.

In accordance with these and other objects of the invention, an assembly is provided which triggers a counting circuit at the point at which the maximum rate of change is observed in the output of a light detector. It has been found that the rate at which a meniscus falls through the field of view of a detector remains constant, within the desired error limits, if temperature and mechanical stability are maintained within certain levels. This allows a more natural and precise triggering point to be determined, specifically the point in time at which the first derivative of the output signal goes through a maximum. It has further been found that the time at which the slope of the output signal reaches a maximum is independent of supply voltage fluctuations. The drawbacks associated with threshold detecting methods are accordingly avoided.

Either of two approaches for defining a triggering point may be used in accordance with the invention. One involves determining the first derivative of the detector output signal and detecting the peak value thereof. In accordance with the preferred embodiment of the invention, a second derivative and zero detection approach are used to define the trigger point.

The apparatus provided in accordance with the invention includes a light detector such as a phototransistor, a first differentiator for providing the first derivative of the output signal from the detector, a counting circuit, and means for triggering the counting circuit when the derivative of the output signal is at its peak. This peak corresponds to the maximum rate of change of the output from the detector.

A second differentiator is preferably employed for providing the second derivative of the output signal. A zero detection circuit is provided for detecting the point at which the value of the second derivative is zero. Means are provided for triggering the counting circuit at this point.

DETAILED DESCRIPTION OF THE INVENTION

Figure 1:
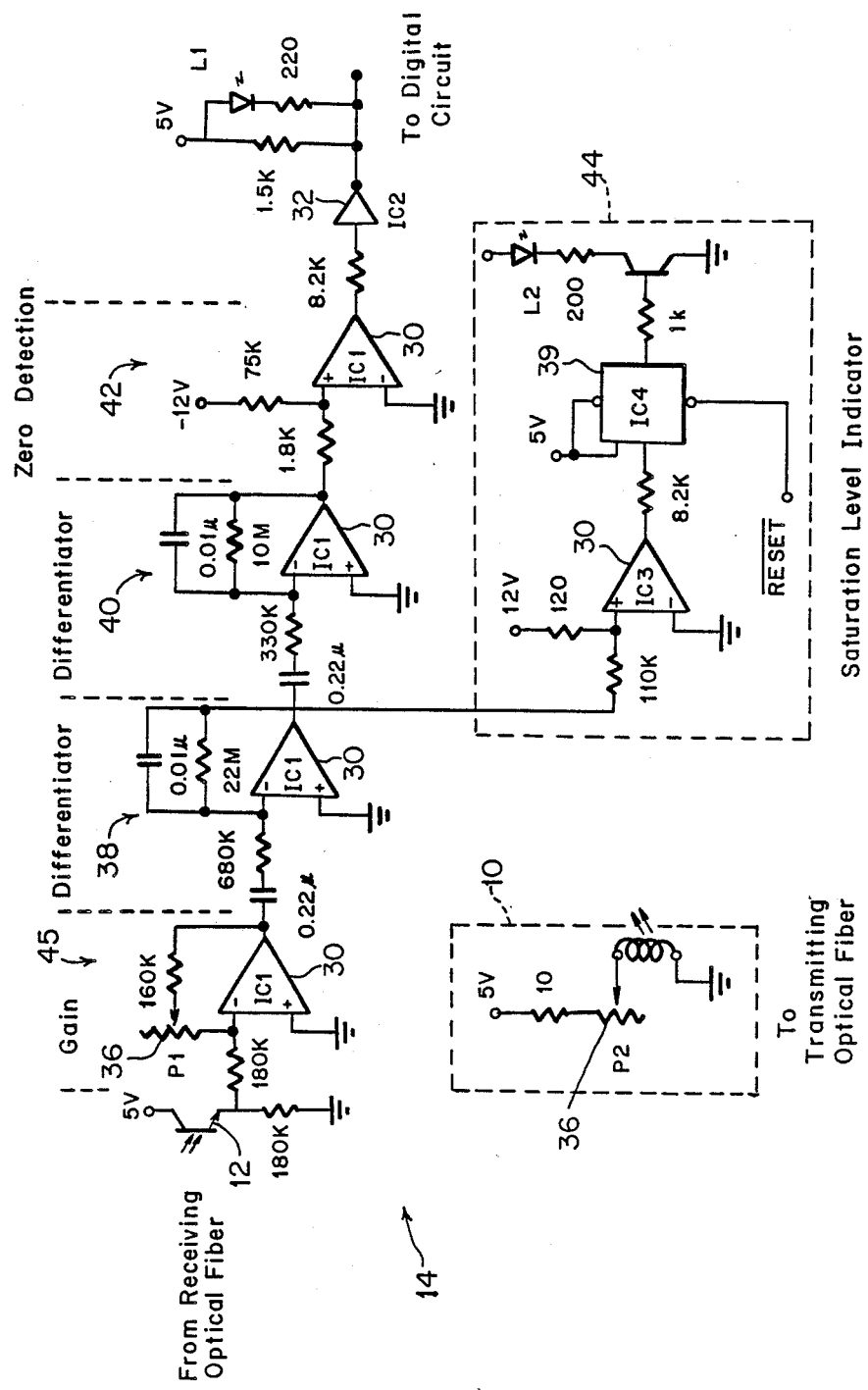
FIG. 1 is an illustration of an analog circuit for producing a start/stop pulse as a meniscus falls through the field of view of a detector.
Figure 2:
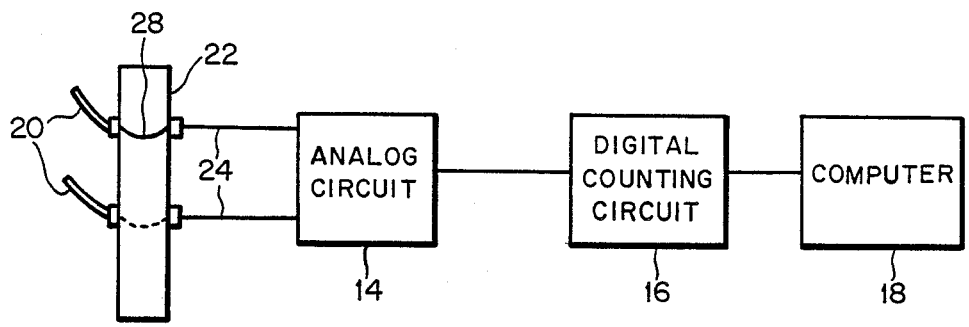
FIG. 2 is a schematic illustration of a capillary viscometer in accordance with the invention.

A method and an apparatus for accurately determining the time take by a liquid meniscus to pass between detection points is provided. The apparatus includes a light source 10 such as a lamp or light emitting diode, a light detector such as a phototransistor 12, an analog circuit 14 for producing triggering pulses, a digital counting circuit 16 for timing the passage of the meniscus between two points, and a computer 18 for calculating the intrinsic viscosity from the data provided by the counting circuit. The apparatus preferably includes two channels for allowing simultaneous tests to be run or for measuring small viscosity differences. FIGS. 1 and 2 illustrate only one of the channels.

Figure 4:
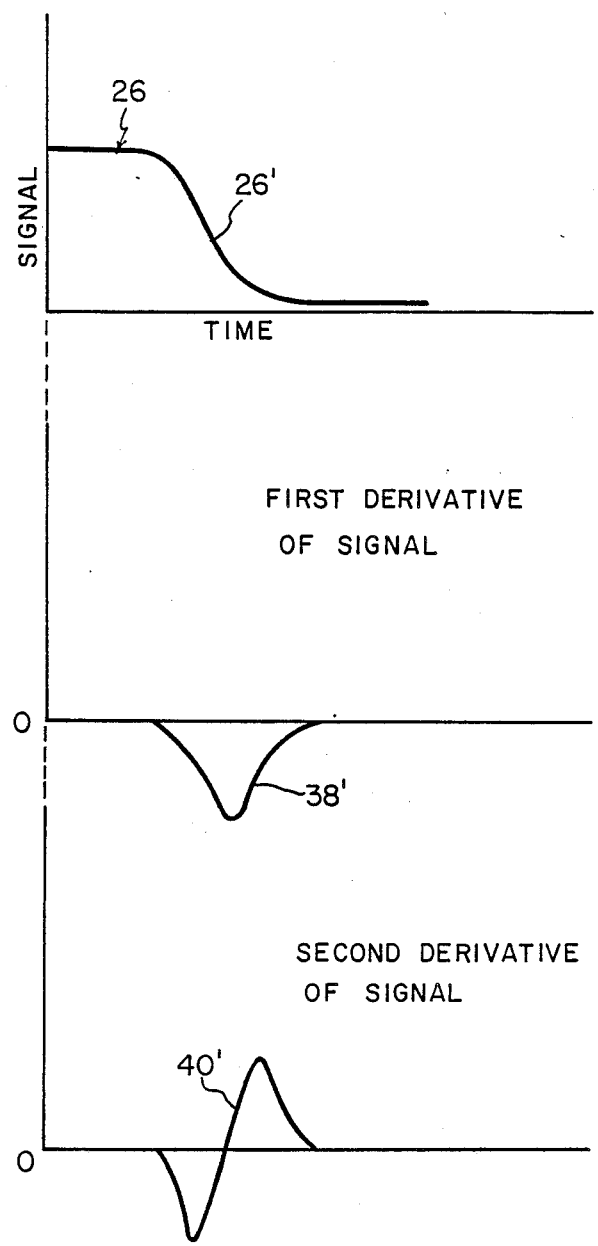
FIG. 4 is a set of three graphs indicating the output signals of a light detector, a first differentiator, and a second differentiator in accordance with the invention.

Referring to FIG. 2, fiber optic bundles 20 are employed for transmitting light from a lamp to a capillary tube 22. Another set of optical fiber bundles 24 detects the scattered light and conveys it to the phototransistor 12. The top graph within FIG. 4 illustrates a typical output signal 26 from the phototransistors, the portion designated by numeral 26' generally illustrating the signal generated as a meniscus 28 falls through the field of view of the detector.

As shown in FIG. 1, the light from one of the detecting bundles is transmitted to the phototransistor 12. The signal produced thereby is processed by the analog circuit to take advantage of the fact that the time at which the slope of the output signal reaches a maximum is independent of supply voltage fluctuations.

The analog circuit 14 includes a plurality of quad operational amplifiers 30, a hex open collector invertor 32, a flip-flop 34, and a fifty ohm trim potentiometer 36. The light source is also regulated by a trim potentiometer. The amplified signal from the phototransistor is differentiated by a first differentiator 38. A second differentiator 40 is provided for taking the second derivative of this signal. The outputs 38', 40' of the first and second differentiators are schematically illustrated in the middle and lower graphs shown in FIG. 4, respectively. A zero detection circuit 42 is provided for detecting the point at which signal from the second differentiator 40 is at zero, which corresponds in time to the peak in the output from the first differentiator 38. A signal (trigger pulse) is generated at this point to start or stop the digital counting circuit 16. Each differentiator is designed to actively differentiate over a very narrow bandwidth in order to provide good noise immunity.

It is important to ensure that the output of the first differentiator never saturates as this will introduce an uncertainty in the position of the trigger pulse. A saturation level indicator 44 and a gain adjustment circuit 45 are accordingly incorporated within the system 14 as a warning indicator and to maximize sensitivity.

Figure 3:
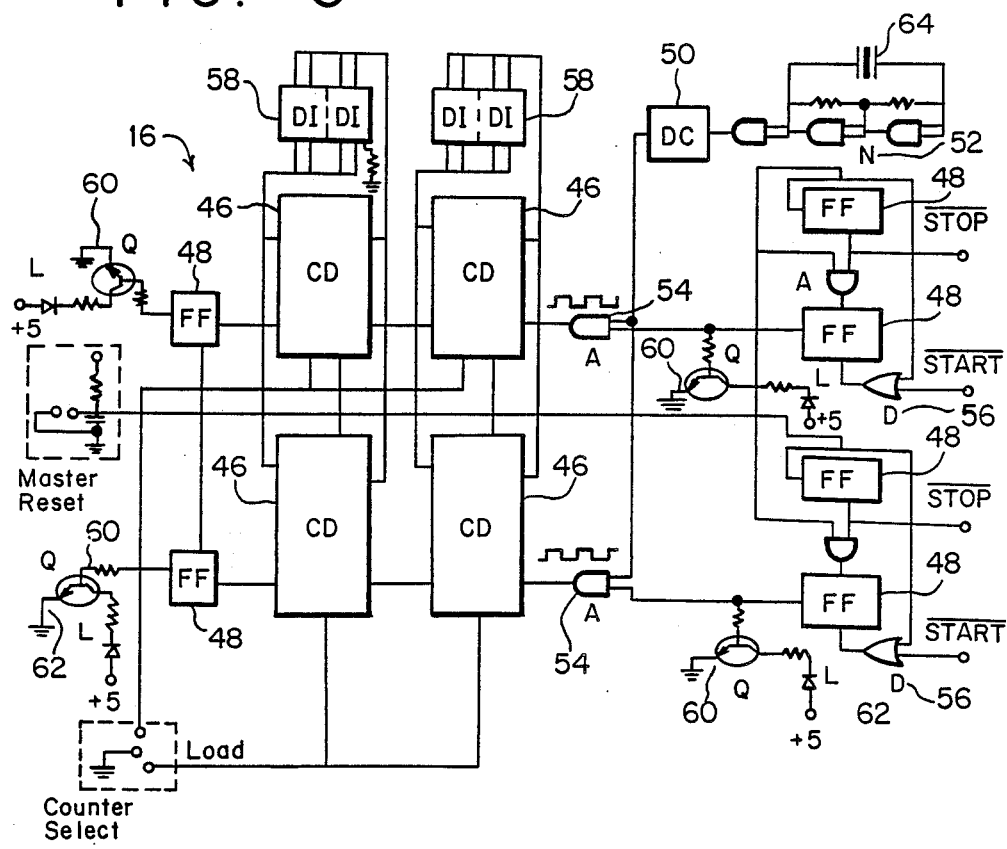
FIG. 3 is a schematic illustration of a digital counting circuit employed.

The digital counting circuit 16 shown in FIG. 3 includes a pair of counting circuits, one for each of the two capillary viscometers employed. It includes two pairs of four-digit counter/drivers 46, six flip-flops 48, a pair 50 of cascaded decade counters, a quad two-input NAND gate 52, two quad two-input AND gates 54, two quad two-input OR gates 56, a pair of drivers 58 (four digits apiece) for a seven segment eight digit display, transistors 60 and light emitting diodes 62. This circuit may be designed by using LSI chips. One main requirement is that it accept separate start and stop pulses for each counter. Another requirement is that it ignore all pulses received after the first start pulse until the system is reset. A one MHz crystal 64 provides the system clock. The pair of cascaded decade counters 50 are used to achieve a 10 kHz clock timer which enables the system to display up to 9999.9999 seconds.

In operation, the viscometer 22 is positioned in a bath maintained at an appropriate temperature to within ± 0.001° C.. It is also supported in a vertical position to within ± 0.05 degrees. A liquid is introduced into the viscometer and allowed to drop therein under the force of gravity. As the meniscus 28 falls through the first field of view of the detector, the signals generated by the phototransistor are processed by the analog circuit 14. Once a zero reading from the second differentiator 40 is detected, a trigger pulse is transmitted to one of the two channels of the counting circuit 16, thereby activating the timer. The timer remains activated until the meniscus approaches the position shown in dotted lines in FIG. 2 and a stop pulse is generated by the analog circuit 14. The stop pulse is generated when a zero reading is again produced by the second differentiator. It has been found that the flow time may be measured to within ± 0.001 seconds, an improvement over conventional methods by about a factor of ten. This allows the intrinsic viscosity of some polymers such as polystyrene in benzene to be estimated to within three percent of the infinite dilution value from a single measurement of specific viscosity at a given polymer concentration over a wide range of molecular weights.

As discussed above, the determination of the intrinsic viscosity has required a series of measurements of specific viscosity at various concentrations when using conventional timing procedures. If the concentration is low enough, the intrinsic viscosity will substantially equal the specific viscosity divided by the concentration. However a lower concentration limit has been imposed by the smallest specific viscosity that can be measured by conventional viscometers. The specific viscosity is directly proportional to the difference in flow times for the solution and the solvent. The difference at relatively low concentrations could not accurately be measured using conventional viscometers having flow time resolutions of ± 0.01 seconds. However, the time resolution of ± 0.001 seconds provided by the invention has allowed intrinsic viscosity to be determined within reasonable boundaries with only a single measurement.

The method according to the invention is applicable to a number of polymers. In a specific test, NBS705 polystyrene dissolved in benzene was utilized at 30° C.. While described in terms of a falling meniscus, the invention would be applicable to systems having a rising meniscus or other moving objects as well. The invention is also applicable to flow time measuring systems which generate output signals having different forms from that disclosed herein, but which may be differentiated to provide a peak. In other words, if the slope of the output signal from a detector reaches a maximum at a certain point, the system according to the invention could be used to provide precise triggering pulses to a timer.

What is claimed is:
1. A capillary tube viscometer comprising:
a tube;
a light source for providing light within said tube;
means for detecting light from said light source;
means for producing a signal upon the detection of light by said light detecting means;
first means for differentiating said signal; means for generating a triggering pulse when the derivative of said signal is substantially peaking;
a timer; and
means for actuating said timer upon the generation of said triggering pulse.
2. A viscometer as defined in claim 1 including second differentiating means for providing the second derivative of said signal; means for detecting when said second derivative has a value of substantially zero, said triggering pulse being generated upon the detection of a substantially zero value of said second derivative of said signal.

3. A viscometer as defined in claim 2 wherein said means for producing a signal upon the detection of light is a phototransistor.

4. A viscometer as defined in claim 3 including a saturation level indicator for indicating whether the output from said first differentiating means is saturated.

5. A viscometer as defined in claim 2 wherein said timer includes a digital counting circuit.

6. An apparatus for determining the flow time for a volume of liquid to pass between two points within a tube, comprising:
   a tube;
   a light source for providing light within said tube;
   first and second means positioned adjacent said tube for detecting light from said light source, said first and second light detecting means being positioned a selected distance from each other;
   means for providing a first signal upon the detection of light by said first light detecting means;
   means for providing a second signal upon the detection of light by said second light detecting means;
   means for providing the first derivative of said first and second signals;
   a timer for measuring said flow time;
   means for providing a triggering pulse to said timer when the first derivative of said first signal or said second signal is substantially peaking; and
   means for starting said timer when said derivative of said first signal is substantially peaking and stopping said timer when said derivative of said second signal is substantially peaking.

7. An apparatus as defined in claim 6 including means for providing the second derivative of said first and second signals; means for detecting when said second derivative has a value of substantially zero; said triggering pulse being generated upon the detection of a substantially zero value of said second derivative of either of said first or second signals.

8. An apparatus as defined in claim 7 wherein said tube is a capillary viscometer tube.

9. An apparatus as defined in claim 8 wherein said means for providing said first signal is a phototransistor.

10. An apparatus as defined in claim 9 wherein said means for providing the first derivative of said first and second signals is a first differentiating circuit.

11. An apparatus as defined in claim 10 including a saturation level indicator for indicating whether the output from said first differentiating circuit is saturated.

12. An apparatus as defined in claim 10 wherein said means for providing the second derivative of said first and second signals is a second differentiating circuit connected in series with said first differentiating circuit.

13. An apparatus as defined in claim 12 wherein said means for detecting when said second derivative has a value of substantially zero is a zero detection circuit connected in series with said second differentiating circuit.

14. An apparatus as defined in claim 8 wherein said timer includes a digital counting circuit.

15. A method for determining the flow time of a liquid between two points within a capillary viscometer tube, comprising:
   introducing a liquid within said tube;
   causing said liquid to flow within said tube in a selected direction;
   introducing light within said tube; detecting said light at a first point within said tube;
   detecting said light at a second point within said tube, said second point being a selected distance from said first point;
   generating a first electric signal corresponding to the intensity of light detected as the meniscus of said liquid passes said first point;
   generating a second electric signal corresponding to the intensity of light detected as the meniscus of said liquid passes said second point;
   differentiating said first electric signal to obtain the first derivative thereof;
   starting a timer when said derivative of said first electric signal is at a peak;
   differentiating said second electric signal to obtain the first derivative thereof; and
   stopping said timer when said first derivative of said second electric signal is at a peak.

16. A method as defined in claim 15 further including the steps of:
   determining the second derivative of said first electric signal;
   detecting when said second derivative of said first electric signal is substantially zero;
   starting said timer when said second derivative of said first electric signal is substantially zero;
   determining the second derivative of said second electric signal;
   detecting when said second derivative of said second electric signal is substantially zero; and
   stopping said timer when said second derivative of said second electric signal is substantially zero.

17. A capillary tube viscometer comprising:
   a tube;
   a light source for providing light within said tube;
   means for detecting light from said light source;
   means for producing a signal upon the detection of light by said light detecting means;
   first means for differentiating said signal;
   second differentiating means for providing the second derivative of said signal;
   means for detecting when said second derivative has a value of substantially zero;
   means for generating a triggering pulse upon the detection of a substantially zero value of said second derivative of said signal;
   a timer;
   means for actuating said timer upon the generation of said triggering pulse; and
   a saturation level indicator for indicating whether the output from said first differentiating means is saturated.

* * * * *